United States Patent [19]

Gavet et al.

[11] Patent Number: 5,009,846
[45] Date of Patent: Apr. 23, 1991

[54] ONE-USE DEVICE FOR BIOLOGICAL TESTS

[75] Inventors: Louis Gavet, Lyon; Roger Chatelin, Lissieu Par; Michel Sotton, St Cyr Au Mont D'Or; Robert Guigal, Lyons; Philippe Laurent, Oullins, all of France

[73] Assignees: Centre Technique Industriel dit: Institut Textile de France; Probiotec (SARL), both of France

[21] Appl. No.: 413,857

[22] Filed: Sep. 28, 1989

[30] Foreign Application Priority Data

Oct. 11, 1988 [FR] France ............................... 88 13668

[51] Int. Cl.$^5$ ..................... G01N 21/00; G01N 31/22
[52] U.S. Cl. ......................................... 422/56; 422/57; 422/58; 422/61; 435/805
[58] Field of Search ....................... 422/56, 57, 58, 61; 435/805; 436/66

[56] References Cited

U.S. PATENT DOCUMENTS 3,043,669  7/1962  Charles ................................. 422/56

Primary Examiner—Robert J. Warden
Assistant Examiner—Thalia P. Vassilatos
Attorney, Agent, or Firm—Ladas & Parry

[57] ABSTRACT

The device comprises at least one element for immobilizing certain molecules contained in the medium to be tested. According to the invention, the immobilizing element is in the form of a hydrophilic material fixed on the surface of a plane hydrophobic material, such as for example viscose fibers (2) implanted by flocking into a sheet (3) of polyvinyl chloride. The device (4) further comprises:

(a) a bottom plate (5) supporting the plane hydrophobic material,
(b) at least one cavity (6) for the liquid medium to be tested, said cavity having an outlet orifice (9) situated above the plane hydrophobic material, and
(c) scraping means (8) acting on the hydrophilic material (1) and capable of moving the liquid contained therein over the surface of the plane hydrophobic material (3).

13 Claims, 1 Drawing Sheet

ONE-USE DEVICE FOR BIOLOGICAL TESTS

FIELD OF THE INVENTION

The present invention relates to one-use devices for carrying out biological tests, including biochemical and alimentary tests, by immobilizing specific molecules contained in the liquid medium to be tested. Such devices are designed in particular for assaying specific molecules, for example in a blood sample.

BACKGROUND OF THE INVENTION

Devices of this type have already been proposed, with the aim of simplifying the work of laboratories and preventing the risks of contamination and inaccurate assaying. In particular, a one-use device for biological tests is described in International Patent Application PCT/US No. 85.00870. This device comprises, on the one hand, an element for immobilizing the molecules, which element is porous and coupled to a sensor of the molecules to be immobilized, and on the other hand, an absorbent material in contact with the lower surface of the immobilizing element. This known device works as follows. The medium to be tested, which contains the molecules to be assayed, is poured over the upper surface of the immobilizing element, diffuses therethrough and, by capillarity, into the absorbent material. The molecules to be assayed are retained by the sensor on the immobilizing element. Thus, the immobilizing element in some way filters the molecules to be assayed, and the absorbent material has the role of speeding up the flow of the medium to be tested through that filter.

SUMMARY OF THE INVENTION

It is now the object of the invention to propose a new one-use device for biological tests. This device comprises at least one element for immobilizing specific molecules contained in a definite volume of a liquid medium. According to the invention, the immobilizing element is in the form of a hydrophilic material fixed on the surface of a planar hydrophobic material, and the device comprises:
(a) a bottom planar supporting the plane hydrophobic material,
(b) at least one cavity for the liquid medium to be tested, said cavity having an outlet orifice situated above the planar hydrophobic material, and
(c) scraping means acting on the hydrophilic material and capable of moving the liquid contained therein over the surface of the planar hydrophobic material.

Thus, contrary to the known device, there is no passage of the medium to be tested through a porous immobilizing element, acting as a filter; and it is no longer necessary to use any absorbent material to speed up the passage though such filter. According to the invention, the medium to be tested contained in the cavity is deposited on the hydrophilic material which is capable of immobilizing the specific molecules; the medium can, optionally, be kept on that material for a predetermined period of time so that said molecules are immobilized in sufficient quantity; then it is extracted and removed from the hydrophilic material by scraping over the surface of the plane hydrophobic material. In a preferred version of the invention, the element for immobilizing the specific molecules is in the form of hydrophilic fibers, implanted substantially vertically in the planar hydrophobic material. For example, the fibers are based on cellulose and the hydrophobic material is based on polyvinyl chloride.

In a first version of the device according to the invention, said device comprises only one immobilizing element, a first cavity for the liquid medium to be tested and at least a second cavity for a reagent, said cavities being situated above the planar hydrophobic material so that, by a relative displacement of the cavities and of the planar hydrophobic material, the hydrophilic material can be placed, successively, under the outlet orifice of the first cavity and then under that of the second cavity, and the scraping means acts on the hydrophilic material after said material has passed under the first cavity. In this case, the reagent contained in the second cavity is deposited on the hydrophilic material in order to reveal the presence of the molecules immobilized thereon and, if necessary, of assaying these molecules.

In a first embodiment of said first version of the device according to the invention, the bottom plate, the cavities and the scraping means are assembled in the form of a box inside which the planar hydrophobic material can move by sliding over the bottom plate.

In a second embodiment of said first version of the device according to the invention, on the one hand, the bottom plate, and on the other hand, the cavities and the scraping means form two separate assebmlies and the device comprises a driving mechanism for driving either one of said two assemblies. In such a case, the relative displacement of the immobilizing element in relation to the cavities is no longer manual but automatic thanks to the driving mechanism.

According to a variant of said second embodiment, the device has an overall circular shape and the driving mechanism drives the assembly composed of the cavities and the scraping means, in rotation about its axis, above the assembly consisting of the bottom plate.

In a second version of the device according to the invention, said device comprises a cavity for the liquid medium to be tested and at least two immobilizing elements, each element immobilizing different molecules, the first element being placed under the cavity containing the liquid medium to be tested, and the second element being at a given distance from the first, and the scraping means is capable of moving the liquid contained in the hydrophilic material of the first immobilizing element, over the surface of the planar hydrophobic material along the given distance up to the hydrophilic material of the second immobilizing element.

BRIEF DESCRIPTION OF THE DRAWINGS

The invention will be more readily understood on reading the following description of three examples of embodiments of the invention, given with reference to the accompanying drawings, in which.

DETAILED DESCRIPTION OF PREFERRED EMBODIMENTS

Figure 1:
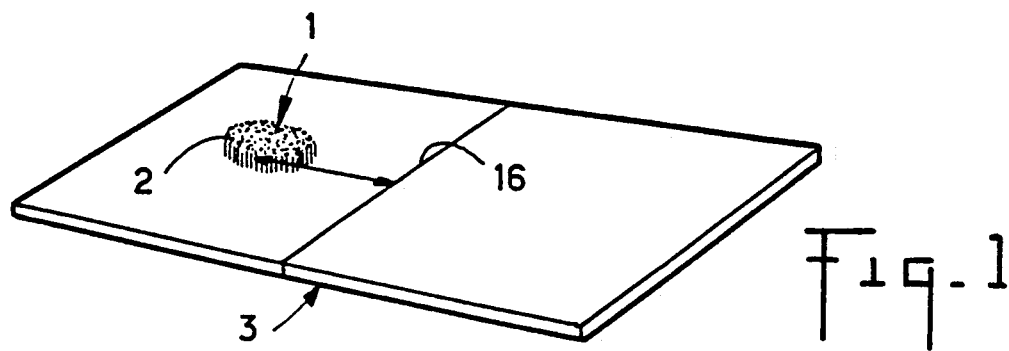
FIGS. 1 and 2 correspond to a first embodiment of the first version of a strictly manual device, FIG. 1 showing the strip supporting the immobilizing element, and FIG. 2 showing a diagrammatical view of a longitudinal section of the device.

In its preferred form, element 1 for immobilizing the specific molecules is in the form of fibers 2 implanted according to the flocking technique in a narrow element or strip. As shown in FIG. 1, the fibers 2 are implanted in circular fashion, in an end zone of the strip 3. Said fibers 2 are made from a hydrophilic material, such as a cellulosic material, and the strip 3 is made from a hydrophobic material, such as polyvinyl chloride.

It is recalled that flocking is a technique conventionally used in the textile industry. It consists for example of spraying the fibers, cut to a set length, onto a substrate in paste state, so that when the substrate has set hard, the base of the fibers is vertically anchored in said substrate. In the present case, the substrate used consists of a 0.9 mm strip 3 of polyvinyl chloride, and the fibers 2 are viscose fibers of 1.7 dtex mean mass per unit length of; fibers 2 protruding from the strip 3 over a height of 0.4 mm.

Figure 2:
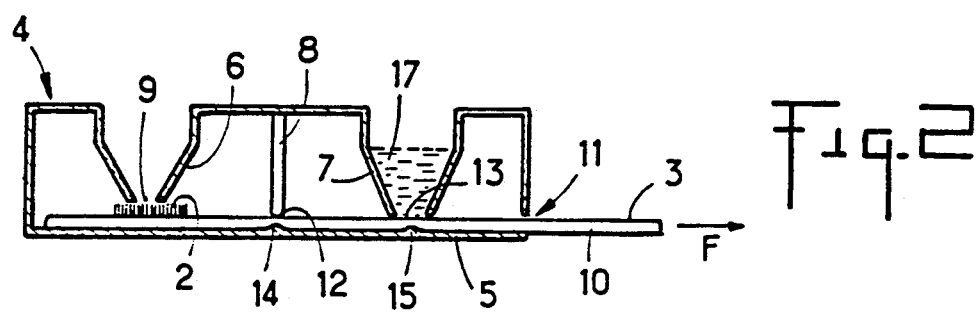

FIG. 2 shows how the strip 3 is placed in the support 4 before use. Said support 4 is a hollow box composed of the following main elements: the lower part which is a rigid flat plate 5; the upper part, namely the part situated above the strip 3, is provided with two cavities 6 and 7 and comprises a rigid inner plate 8 situated between the two cavities 6 and 7.

Positioning of the strip 3 inside the support 4 before use is as follows: the lower face of the strip 3 rests on the bottom plate 5; the end zone of the strip 3 where the circular patch 1 of fibers 2 is implanted, is placed under the cavity 6 so that the orifice 9 of the cavity 6 is situated just above said patch 1; the end zone 10 of the strip which is in opposite relation to the patch zone projects from the support 4 through a slot 11. Plate 8, placed immediately after cavity 6, has a rectilinear border 12 which is applied against the upper face of the strip 3. Orifice 13 of cavity 7 is applied against the upper face of the strip 3 between the plate 8 and the outlet slot 11.

The bottom plate 5 may comprise, in facing relationship to the edge 12 of the plate 8 and to the orifice 13 of the second cavity 7, bosses 14 and 15.

For simplification purposes, the support has been described to have two cavities, but the device according to the invention may comprise a higher number of these, as a function of the number of reagents required for carrying out the assay.

The fibers 2 are treated beforehand so that they can immobilize the specific molecules, as a function of the assay to be effected, for example by grafting active centers capable of interacting with said molecules by exchange of ions or by formation of covalent bonds.

In the case of assaying immunoglobulins in human serum, the viscose fibers 2 are grafted before being implanted in the strip 3, by subjecting them successively to a controlled impregnation with a 20% aqueous solution of 2-acrylamido-2-methyl propane sulfonate, to irradiation by an electron beam at a dose of 2 Mrad, followed by rinsing and drying. The cellulosic structure of the viscose comprises grafts which are carriers of sulfonic functions.

For assaying, a predetermined volume of the biological medium to be tested, for example serum, is introduced in the first cavity 6. The hydrophilic fibers 2 absorb entirely the introduced volume. The sulfonic functions carried by the grafts on the grafted viscose immobilize, by ionic interaction, the proteins situated in the serum in macro-ions state. The protein-fixing kinetics and the proportion of fixed proteins vary with the serum and the pH. It is found, after a five-minute contact period, that 90% of the human immunoglobulins (IgG, IgM, IgA) has been immobilized, regardless of the pH. The total protein concentration was measured by the Bradford method; it was found to be between 350 and 400 mg of proteins in 0.2 ml of reaction medium.

After a period long enough to allow the immobilization of the molecules on the fibers 2, the strip 3 is caused to slip on the bottom plate 5 by pulling on the end part 10 extending from the support 4, until the mark 16, made on the upper face of the strip 3, is level with the slot 11. Said mark 16 is for example a transversal line, spaced from the center of the circular patch 1 of fibers 2 of a distance $\underline{h}$ corresponding to the spacing between the orifice 13 of the second cavity 7 and the slot 11. Thus, when the line 16 is perpendicular to the slot 11, the patch 1 is under the orifice 13 of the second cavity 7.

When the strip 3 is moved in the direction of arrow F shown in FIG. 2, the fibers 2 pass between the lower edge 12 of the plate 8 and the bottom plate 5; plate 8 then acts as a scraper, compressing the fibers 2 and mechanically extracting the liquid contained therein. The extracted liquid flows over the hydrophobic surface of the strip 3 and remains in the hollow part of the support situated between the cavity 6 and the plate 8.

The movement of the strip continues until the patch 1 is situated under the second cavity 7.

The reagent 17, which is present or introduced in the second cavity 7 is absorbed by the liquid-free hydrophilic fibers 2, and reacts with the immobilized molecules.

Understandably, the initial liquid has to be extracted from the fibers 2 so that said fibers can absorb another quantity of reagent 17. Of course, in the case of a strictly mechanical extraction, the fibers 2 are not properly dry, and still contain the water retained by hydrogen bond and capillarity, nevertheless they have retained a high power of absorption.

The presence of bosses 14 and 15 in facing relationship on the bottom plate 5, respectively, to the plate 8 and to the second cavity 7, contributes to improving, among other things, the tightness of the device, among other things. The planar hydrophobic material constituting the strip 3 is preferably a material with a certain elasticity, which is precisely the case of polyvinyl chloride. The bosses 14 and 15 slightly compress the strip 3 when this strip is at right angle with the plate 8 and the second cavity 7.

On the one hand, the scraping action of plate 8 is combined with a squeezing by compression; on the other hand, the strip 3 is constantly applied against the lips of the orifice 13 of the second cavity 7. It is then possible to store the reagent 17 in the cavity 7 of the device before use, without any danger of said reagent flowing inside the support 4, the cavity 7 being sealed by the application of the hydrophobic strip 3 against orifice 13.

Therefore, before use, the device is presented in the form of a box inside which the strip 3 is in position, with the portion 10 extending through the opening 11, and the second cavities 7 are filled with the reagents 17 and sealed off by a plastic film.

Figure 3:
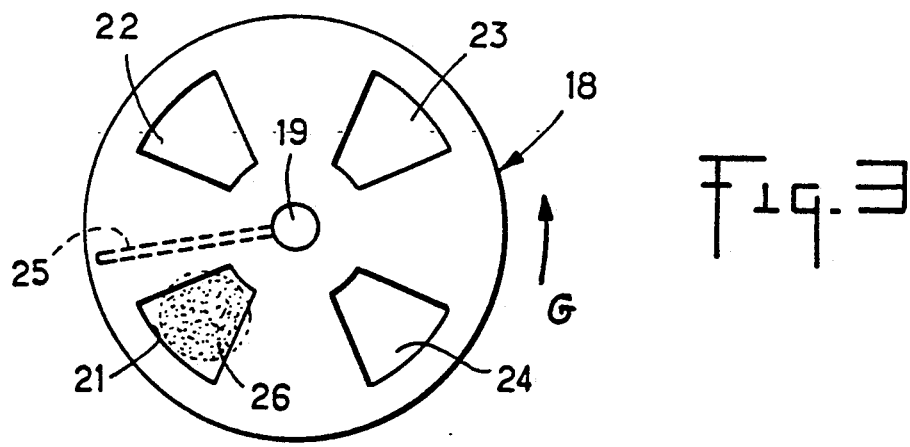
FIG. 3 corresponds to a second embodiment of the first version of a device working automatically, and shows a diagrammatical plan view of said device.

According to the second embodiment of the invention, illustrated in FIG. 3, the device has an overall circular shape; the upper part, containing the cavities for receiving the medium to be tested and the reagents, is movable with respect to the bottom plate, according to a rotary movement about the pin 19 in the direction of arrow G. The device 18 illustrated in FIG. 3 has four cavities, the first one 21 destined to receive the medium to be tested, the others 22, 23 and 24 destined to receive or to store the various reagents. The plate 25 for scraping the liquid contained in the hydrophilic fibers of the patch 26 is radially mounted, being fast with the upper part of the device, between the first two cavities 21 and 22.

The device comprises, under the bottom plate, a driving mechanism, not shown, for driving the pin 19, which is itself fast with the upper part. Said mechanism, equipped for example with a winding key, permits the driving of said upper part in rotation about pin 19 according to a present sequence. Thus, in this second embodiment, the device does not work entirely by hand, it is also partly automatic.

The planar hydrophobic material is fixed on its support plate and it is the cavities 21–24 and the scraping plate 25 which move above said hydrophobic material by rotation about pin 19. The mechanism is programmed so that the speed of rotation corresponds to the contact time required, on the one hand, for immobilizing the specific molecules on the hydrophilic material 26 and, on the other hand, for the subsequent action of the reagents.

Figure 4:
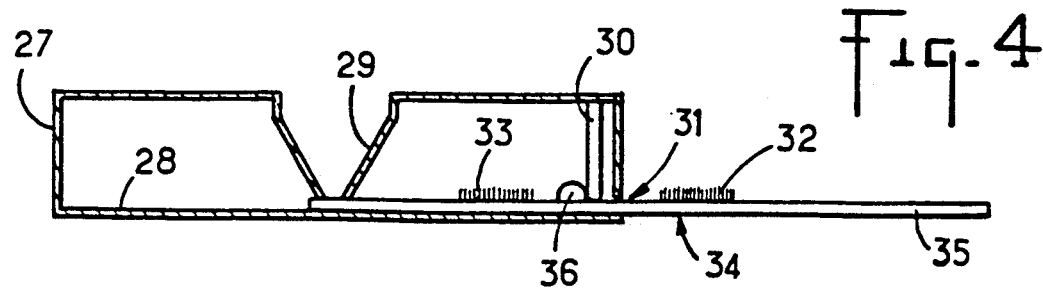
FIG. 4 corresponds to the second version of a strictly manual device, and shows a diagrammatical view of a longitudinal section of the device, when in use.

According to the third embodiment of the invention, illustrated in FIG. 4, the support 27 is a hollow box composed of a lower part which is rigid flat plate 28 and of an adjoining upper part which is provided with a substantially central cavity 29 and comprises an inner rigid plate 30 placed proximate to the edge comprising a slot 31 along the plate 28.

The planar hydrophobic material is, similarly to that of the first embodiment, a strip 34, with the exception that this strip is provided on its surface with two zones 32 and 33, comprising a hydrophilic immobilizing material.

Before use, the first zone 32 is situated under the cavity 29, containing already, or due to receive the liquid medium to be tested. Once the liquid has been absorbed by the hydrophilic material of the first zone 32 and the specific molecules have been immobilized by said material, the strip 34 is caused to slide by pulling on the end 35 projecting out of the box 27 through the slot 31. During the displacement of the strip, the first zone 32 passes under the plate 30 which scrapes the corresponding hydrophilic material and extracts mechanically the liquid contained therein and which is free of the specific molecules; the pulling action being continued, the liquid, for example in the form of a drop 36, as illustrated in FIG. 4, is kept by the plate 30 on the surface of the hydrophobic strip 34; the pulling action on the strip is discontinued when the liquid 36 reaches the level of the second immobilizing zone 33 where it is absorbed by the hydrophilic material.

In this case, it is in the second zone 33 that the reaction necessary to the test takes place. For example, the hydrophilic material of said second zone 33 contains immobilized enzymes capable of picking up molecules of the liquid 36 after its passage over the first zone 32, and of producing an enzymatic reaction which can be detected for example by a chromogenic substance. Said chromogenic substance can optionally be introduced into the cavity 29 with the liquid medium to be tested.

For example, glucose in the blood has been tested with grafted viscose fibers in the first zone 32, the grafts of said fibers carrying sulfonic groups, capable of immobilizing proteins, and in the second zone 33, fibers on which is fixed the glucose oxidase, which is an enzyme fixing the glucose.

The invention is not in any way limited to the three above-described embodiments, and on the contrary covers many variants.

The presentation of the hydrophilic material in the form of fibers flocked in a hydrophobic material is particularly advantageous in that the particular disposition of the fibers offers a large fiber surface with respect to the liquid medium, but other presentations may be used, such as for example loop piles, or terrycloth piles, etc.

The function of the hydrophilic material is to immobilize certain molecules. This is achieved, depending on the type of molecules, by any suitable way: covalent bonds, complexing, ion exchanges. It is then left to the person skilled in the art to select the constituents of said hydrophilic material, or to carry out the adequate treatments in order to obtain the required immobilization.

One particular example of such treatments is the technique consisting of grafting on the polymer structure of the hydrophilic material a graft carrying functional groups capable of picking up the definite molecules. The positioning of the functional groups on grafts improves the accessibility of the molecules and the molecules' immobilization kinetics. Moreover, the immobilizing effect is permanent because the functional groups are attached by covalent bonds.

The invention finds its preferred application in the field of biological tests, where quick and reliable assaying methods are sought and where a one-use device presents numerous advantages; nevertheless, the device can also be used in other fields, without departing from the scope of the invention, for example in everyday chemical analyses.

Assaying may be carried out from molecules immobilized on the immobilizing element, as described hereinabove; but it can also be performed, without departing from the invention, on the liquid medium wherefrom the said molecules have been extracted and which is removed from the hydrophilic material by scraping. In this case, the device comprises means for recovering the liquid medium, such as for example a cavity formed in the bottom plate at the front of the scraping means in the first embodiment.

What is claimed is:

1. A unitary, one-use device for biological tests comprising:
   (a) at least one element for immobilizing specific molecules contained in a liquid medium to be tested, wherein said immobilizing element is in the form of a hydrophilic material;
   (b) a planar hydrophobic material on a surface of which is fixed said immobilizing element;
   (c) a bottom plate supporting the planar hydrophobic material;
   (d) at least one cavity for a liquid medium to be tested, said cavity having an outlet orifice situated above the planar hydrophobic material, and
   (e) a scraping means situated above said planar hydrophobic material;
   whereby said immobilizing element, said planar hydrophobic material, said bottom plate, said cavity for a liquid medium to be tested, and said scraping means are capable of interacting in the unitary device so that when liquid medium is introduced into the cavity, it exits the cavity through the outlet orifice to contact the hydrophilic material of the 2. Device as claimed in claim 1, wherein the immobilizing element is in the form of hydrophilic fibers implanted substantially vertically in the planar hydrophobic material.

3. Device as claimed in claim 2, wherein the hydrophilic fibers are viscose fibers implanted by flocking in a sheet of polyvinyl chloride.

4. Device as claimed in claim 1, wherein said device further comprises at least another cavity for a reagent, said cavities being situated above the planar hydrophobic material so that, by a relative displacement of the cavities and of the planar hydrophobic material, the hydrophilic material can be placed, successively, under the outlet orifice of the one cavity and then under an outlet orifice of said another cavity, and the scraping means acts on the hydrophilic material after said material has passed under the one cavity.

5. Device as claimed in claim 4, wherein the bottom plate, the cavities and the scraping means are assembled in the form of a box inside which the planar hydrophobic material can move by sliding over the bottom plate.

6. Device as claimed in claim 4, wherein on the one hand the bottom plate and on the other hand the cavities and the scraping means form two independent assemblies and wherein said device comprises a driving mechanism causing the relative displacement of one of said two assemblies with respect to the other.

7. Device as claimed in claim 5, wherein the device has an overall circular shape and the driving mechanism drives the assembly composed of the cavities and the scraping means, in rotation about its axis, above the assembly comprising the bottom plate.

8. Device as claimed in claim 1, wherein the scraping means is a rigid plate of which the lower edge is applied on the planar hydrophobic material supported by the bottom plate.

9. Device as claimed in claim 1, wherein said device further comprises at least another element for immobilizing different molecules, the one element being placed under the cavity containing the liquid medium to be tested, and said another element being at a given distance from the one element, and the scraping means positioning over the planar hydrophobic material and being capable of moving the liquid contained in the hydrophilic material of the one immobilizing element along the given distance up to the hydrophilic material of said another immobilizing element.

10. Device as claimed in claim 1, wherein the immobilizing element comprises a polymeric structure on which are grafted grafts which are carriers of functional groups capable of sensing the specific molecules.

11. A method for assaying immunoglobulins by using the device of claim 1, comprising the steps of:
grafting cellulosic fibers of a hydrophilic material as an immobilizing element before implanting the same on a planar hydrophobic material strip which is in turn supported by a bottom plate;
introducing a biological medium to be tested into one cavity situated above the hydrophilic fibers wherein said medium is absorbed entirely by the fibers;
moving the hydrophilic fibers, as treated after a period long enough to allow the immobilization of the hydrophilic material, away from the one cavity to another cavity containing reagent, a scraping means provided to compress the hydrophilic material and extract the liquid contained therein during the moving thereof.

12. A method according to claim 11, further comprising a step of grafting another immobilizing element containing an enzyme capable of producing an enzymatic reaction for biological assays on the hydrophobic material.

13. A method according to claim 12, wherein the one immobilizing element is capable of immobilizing the proteins and said another immobilizing element contains glucose oxidase for the purpose of assaying glucose in the blood.

* * * * *